US008744793B2

(12) United States Patent
McKeon

(10) Patent No.: US 8,744,793 B2
(45) Date of Patent: Jun. 3, 2014

(54) METHOD AND APPARATUS FOR ADJUSTING THE LEVEL OF A RESPONSE SIGNAL FROM AN ULTRASOUND TRANSDUCER

(75) Inventor: James C. P. McKeon, Woodbridge, VA (US)

(73) Assignee: Sonix, Inc., Springfield, VA (US)

( * ) Notice: Subject to any disclaimer, the term of this patent is extended or adjusted under 35 U.S.C. 154(b) by 305 days.

(21) Appl. No.: 13/240,273

(22) Filed: Sep. 22, 2011

(65) Prior Publication Data

US 2012/0101764 A1 Apr. 26, 2012

Related U.S. Application Data

(60) Provisional application No. 61/394,857, filed on Oct. 20, 2010.

(51) Int. Cl.
G10K 15/04 (2006.01)
G10K 11/00 (2006.01)
G01H 17/00 (2006.01)
A61B 8/00 (2006.01)
A61B 8/12 (2006.01)

(52) U.S. Cl.
CPC *G01H 17/00* (2013.01); *A61B 8/00* (2013.01); *A61B 8/12* (2013.01); *A61B 8/4281* (2013.01)
USPC .............................. 702/103; 600/437; 702/159

(58) Field of Classification Search
CPC ............ G01H 17/00; A61B 8/00; A61B 8/12; A61B 8/4281; B06B 1/0207
USPC ............... 702/16, 39, 85, 103, 116, 118, 119, 702/159, 180; 600/437, 442, 443; 73/589, 73/602, 627
See application file for complete search history.

(56) References Cited

U.S. PATENT DOCUMENTS

| 4,518,992 | A | 5/1985 | Kessler et al. |
| 5,511,425 | A | 4/1996 | Kleinert et al. |
| 5,524,626 | A | 6/1996 | Liu |
| 5,676,149 | A * | 10/1997 | Yao .............................. 600/437 |
| 6,374,675 | B1 | 4/2002 | DePetrillo |
| 6,880,387 | B2 | 4/2005 | Kessler et al. |
| 6,895,820 | B2 | 5/2005 | Oravecz et al. |
| 7,000,475 | B2 | 2/2006 | Oravecz et al. |
| 7,013,732 | B2 | 3/2006 | McKeon |
| 7,787,680 | B2 | 8/2010 | Ahn et al. |

(Continued)

OTHER PUBLICATIONS

PCT International Search Report and Written Opinion, PCT Appl. PCT/US2011/052736, mailed from KIPO on Apr. 27, 2012.

*Primary Examiner* — John H Le

(57) ABSTRACT

A method and apparatus for dynamically adjusting the level of a response signal from an ultrasound transducer is disclosed. During a calibration phase, a description of a gain profile of a level adjuster is set dependent upon an expected response signal for a type of object to be tested and the description is stored in memory. During a measurement phase for an object under test, a description of a gain profile is selected for the type of the object under test and a gain profile is determined from the selected description. The response signal from the object under test is passed through a level adjuster and the level of the response signal is adjusted dynamically in accordance with the gain profile. The description of the gain profile is selected with reference to an expected response either by operator interaction with a user interface or automatically.

40 Claims, 12 Drawing Sheets

(56) References Cited

U.S. PATENT DOCUMENTS

| | | | |
|---|---|---|---|
| 8,568,319 B1 * | 10/2013 | Kaplan et al. | 600/437 |
| 2003/0023393 A1 | 1/2003 | Oravecz | |
| 2005/0229707 A1 | 10/2005 | Oravecz et al. | |
| 2006/0272419 A1 | 12/2006 | Maris et al. | |
| 2008/0006091 A1 | 1/2008 | McKeon | |
| 2009/0062648 A1 | 3/2009 | Derby | |
| 2009/0069682 A1 | 3/2009 | Hastings et al. | |
| 2009/0095086 A1 | 4/2009 | Kessler et al. | |
| 2010/0174190 A1 | 7/2010 | Hancock et al. | |

* cited by examiner

METHOD AND APPARATUS FOR ADJUSTING THE LEVEL OF A RESPONSE SIGNAL FROM AN ULTRASOUND TRANSDUCER

PRIORITY CLAIM

This application claims priority to U.S. Provisional Patent Application No. 61/394,857 filed Oct. 20, 2010, which is hereby incorporated herein by reference.

BACKGROUND

The use of time gain control (TGC) in medical ultrasonic imaging and non-destructive testing is well known. In ultrasonic imaging, pulses of acoustic energy reflected from or transmitted though an object are measured and processed to produce images of the object. As an ultrasonic pulse propagates through an object it is generally subject to attenuation due to a variety of physical mechanisms. Generally, the amount of attenuation increases with the length (in time or distance) the propagation path. Thus, for example, a reflection from impedance mismatch deep in an object is generally at a lower level than a reflection from a similar impedance mismatch nearer the surface.

Measurement systems used to capture the reflected or transmitted sound are imperfect. In particular, they have limited dynamic range and limited resolution.

The effect of limited dynamic range may be mitigated by using non-linear signal compression to boost low level signals relative to high level signals before the signals are captured.

A further approach is to use a variable gain amplifier to increase the gain of the signal path over time, as the signal level decreases. This approach has been used successfully in ultrasound systems for imaging bulk materials. In this application, the decrease of the signal strength with time is largely due to geometric spreading and absorption in the material. Thus, the gain of the variable gain amplifier is generally increased with time in a simple geometric and/or exponential manner.

This approach has also been used successfully in medical ultrasound. In medical ultrasound, an image is captured using arrays of transmitting and receiving transducers, together with phased-array beamforming.

The structure of the part of the body being scanned is complicated and three-dimensional, so again the gain of the variable gain amplifier is generally increased with time in simple geometric or exponential manner defined by a single parameter that may be adjusted by an operator. For example, the operator may view repeated C-scan displays, adjusting the parameter between scans to obtain an image that appears to be improved.

BRIEF DESCRIPTION OF THE FIGURES

The accompanying figures, in which like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
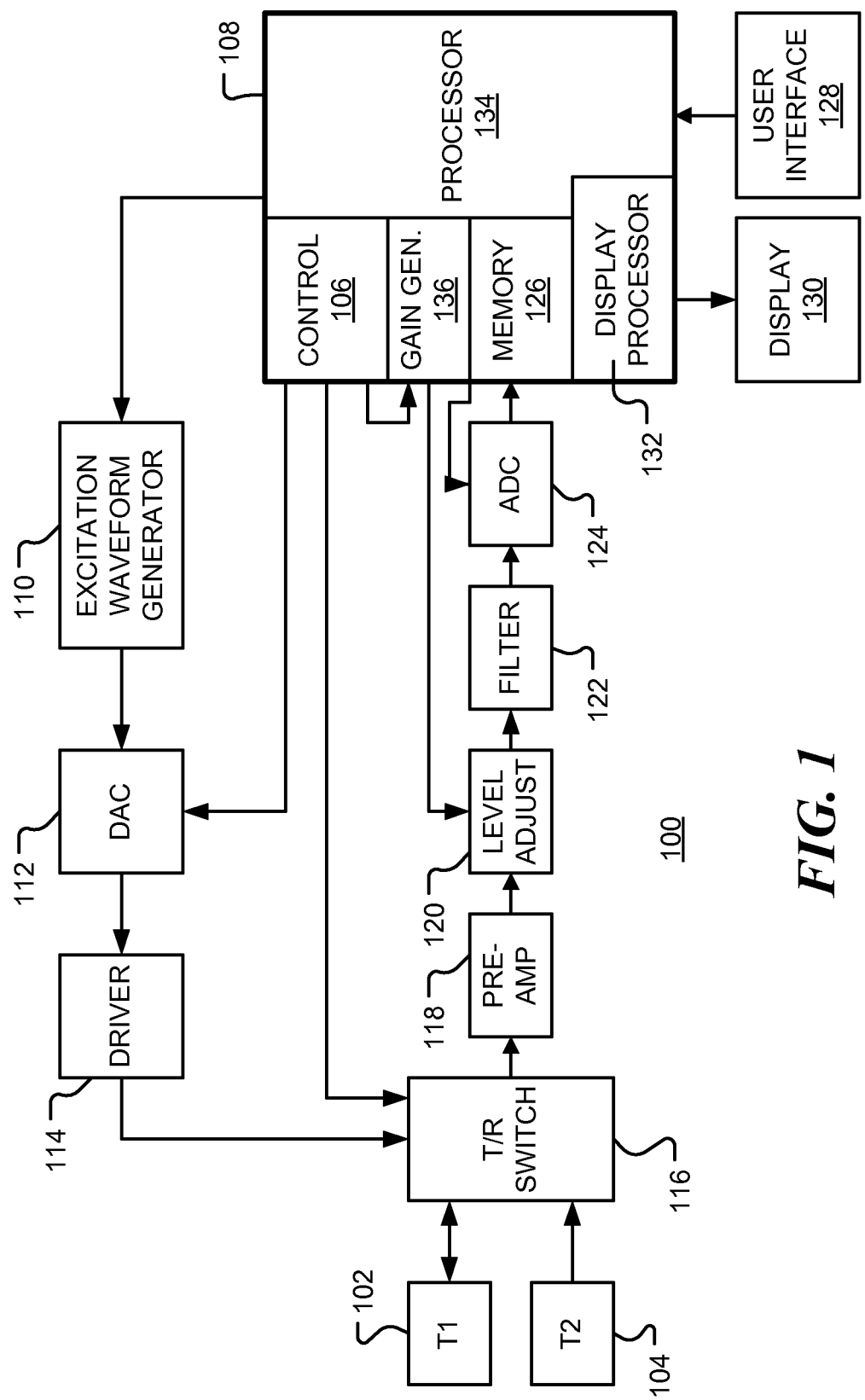
FIG. 1 is a block diagram of an exemplary ultrasound system in accordance with some embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to dynamic level adjustment of an ultrasonic response signal. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Ultrasonic imaging of electronic components may be performed, for example, by a scanning acoustic microscope (SAM). A SAM forms images of electronic components or other objects by moving a transducer across the component in a scan path and generating ultrasonic pulses at a number of different positions.

The structure of many electronic components is substantially laminar, since components may be constructed in layers. For example, multiple silicon dies may be stacked, one on top of the other to form a stacked die package. In a stacked die package, such as an SiP (System in Package), stacked die memory, or CoC (Chip on Chip) package, two or more integrated circuits are installed on top of one another. This allows a higher density of components. Molded flip chips also tend to have a laminar structure. Flip chip packaging, also known as 'Controlled Collapse Chip Connection' or its acronym, C4, is a method for interconnecting semiconductor devices, such as IC chips and micro-electro-mechanical systems (MEMS), to external circuitry with solder bumps that have been deposited onto the chip pads. The solder bumps are deposited on the chip pads on the top side of the wafer during the final wafer processing step. In order to mount the chip to external circuitry (e.g., a circuit board or another chip or wafer), it is flipped over so that its top side faces down, and aligned so that its pads align with matching pads on the external circuit, and then the solder is flowed to complete the interconnect. Even single integrated circuits often have multiple layers.

Examples of other objects that may be tested include:
(1) Lidded flip-chips. Using dynamic level adjustment, ultrasound is able to penetrate the lid and lid attachment to enable imaging of the die top and die attachment in a single scan.
(2) Bare flip-chips. Dynamic level adjustment facilitates substrate inspection of bare flip chips, in which the flip-chip under-fill, solder bumps and substrate layers are imaged in a single scan
(3) Three dimensional integrated circuit packages. In these packages bare die are stacked on top of each other. Dynamic level adjustment facilitates the imaging of die interconnections, such as TSV (through silicon vias), and other features.
(4) MEMS capacitors.

These structures have increased depth compared with single integrated circuit chips components, and are more difficult to image because of increased ultrasound attenuation with depth and loss of signal strength due to multiple transmissions and reflections at impedance mismatches within the component. In accordance with one aspect of the invention, it is recognized that the gain-time profile of a level adjuster in the receive signal path of an ultrasound system, such as a scanning acoustic microscope, may be selected in accordance with the general structure of the object under test. The gain applied to a response signal from a single excitation pulse is controlled over the duration of the response in accordance with the gain-time profile to improve the performance of the ultrasound system.

This approach enables ultrasound from different regions within an object under test to be analyzed using a single pulse. Previously, the gain was set for each region in turn, requiring multiple pulses or scans to be performed and resulting in longer scan times.

The gain-time profile specifies the gain (which may be less than unity) applied to the response signal by the level-adjuster as a function of time. Thus, the gain is adjusted dynamically. Time may be measured from the time at which an excitation signal is generated by an ultrasonic transducer, or from the time at which a first reflection is received (such as the reflection from the nearest surface of the object under test), or some other reference time. The level adjuster in the receive path enables dynamic adjustment of the level of a response signal from an ultrasound transducer. Hereafter, the 'gain-time profile' will be referred to simply as the 'gain profile', but it is to be understood that the gain profile is applied under timing control.

In a measurement phase, a multi-layered object under test is imaged by exciting the multi-layered object with a pulse of ultrasound at a first time and sensing ultrasound produced by the multi-layered object in response to the pulse of ultrasound to obtain a response signal. For each of a plurality of second times, subsequent to the first time, the level of the response signal is adjusted in accordance with a gain profile, to obtain a level adjusted response signal. The plurality of second times corresponds to expected times of flight of ultrasound from layers of the multi-layered object. The time of flight, or propagation time, is the time it takes for ultrasound to propagate from the ultrasound source, interact with the object under test, and return to the ultrasound receiver. The level adjusted response signal is sampled to obtain a sampled response signal, which is then processed to obtain ultrasound images of the layers of the multi-layered object.

In the measurement phase, the response signal from the object under test is passed through a level adjuster, causing the level of the response signal to be adjusted in accordance with the gain profile. A description of a gain profile may be selected in accordance with the object under test from one or more gain profile descriptions. The gain profile is determined from the selected description of a gain profile.

The description of the gain profile of the level adjuster may be set in a calibration phase, dependent upon an expected response signal for an object to be tested, and stored in a memory or other computer readable medium.

One embodiment of the invention comprises a gain control circuit board that is added into a controller for an ultrasonic inspection system and user interface software that is executable on a processor of the controller. The gain control circuit board and the accompanying user interface enable a user to create a gain profile that varies over the duration of a response as opposed to a flat gain curve in typical ultrasonic and Scanning Acoustic Microscopy (SAM) systems.

A gain profile may be set by user interaction with the user interface that enables the user to change the gain setting up or down at specific time instances. For example, the gains may be selected to equalize sections of the response signal due to reflections from different interfaces within a multilayered sample. This, in turn, allows for the imaging of features and defects specific to each of the many layers in a single scan. With a traditional system, the user often has to perform multiple scans at either different focus (z-axis) positions or gain settings in order to see all of the interfaces in a multi-layered object, and in any one of these traditional scans deeper interfaces will either be too dark or earlier interfaces will be too bright (saturated) for inspection purposes.

Previously, gain control such as TGC (time gain compensation) or DAC (Distance Amplitude Correction) has been used in ultrasonic systems that inspect bulk (single layer) materials. In these cases, the user is trying to equalize sections of the response signal due to reflections from defects (voids/porosity or inclusions) at different depths within the single bulk material, so that a single pass/fail threshold may be used over the whole depth of the material. The bulk materials used are often much thicker than the multilayered samples and therefore much lower ultrasonic frequencies (0.5-15 MHz), lower bandwidth TGC or DAC circuits (1-20 MHz), and slower gain profile reaction times are used.

In contrast, the present invention enables the imaging of reflections from the many layers of a microelectronics sample. In this application, the reflections will often occur faster than the gain profile reaction time of a TGC or DAC circuit. In one embodiment of the present inventions, higher ultrasonic frequencies (5-300 MHz), higher bandwidth (1-500 MHz), and much faster circuit reaction times are used.

The description of a gain profile of the level adjuster may be set by displaying the expected response signal to a user, processing user input via a graphical user interface to select time values and to select corresponding gain values to be applied at the selected time values. The time values and corresponding gain values provide a description of the gain profile and may be stored in a computer memory, for example, In one embodiment, the description of the gain profile in a memory comprises storing a lookup table of gain values indexed by time values.

The graphical user interface may comprise a data entry form or a graphical display of the gain profile, for example.

The invention has application to the ultrasonic inspection of electronic components and, in particular, to multi-layer devices. In the manufacture of such devices, multiple devices of the same type are often manufactured. The type of the device, or other objects, to be imaged may be indicated by an identifier, such as a number or name, which is used to select the gain profile to be used when scanning that type of device or object.

Commonly, the desired structure of an object to be imaged is known in advance. In such applications, the expected response signal may be computed using a computer simulation of the type of object to be tested. Alternatively, the expected response may be obtained by measuring the response signal from an object of the type of object to be tested. Once the expected response is known, the gain profile may be set. For example, the gain in the time region of one or more reflections may be selected to equalize the amplitude of the reflection. The simulation may include estimating responses from signal paths that include multiple internal reflections.

The response signal may be sampled to obtain a sampled response signal. In this case, the level of the response signal is adjusted before the response signal is sampled. For example, the level adjuster may be positioned in the signal path before an analog-to-digital converter (ADC). This allows multiple reflections to be sampled with similar digital resolutions, and allows multiple layers within the object to be scanned using the same excitation pulse.

In an alternative embodiment, the level adjustment is performed after response signal has been sampled.

The gain at each time value may be set by user interaction with a graphical interface to the computer, or the gain may be set automatically to achieve a predetermined signal level.

In a given system, the achievable gain profile may be subject to physical constraints, such as the maximum gain, the maximum rate of change of gain or the minimum delay between a trigger time and the application of the gain. The gain profile is set subject to these constraints.

In an embodiment where the description of the gain profile comprises a set of time values and a set of gain value to be applied at those time values, the gain profile at other times may be obtained interpolating between the set of gain values Gain profile descriptions may be distributed to scanning system via a network, such as the Internet. This is useful, for example, when the gain profile descriptions are obtained from computer simulations that may performed at a remote location.

Gain profile descriptions may also be distributed by other means, such as computer discs, flash memory devices or other computer readable media. Gain profiles distributed in this way may be copied to local storage media of the scanner's computer.

The scan path of a SAM is often substantially parallel to the laminar structure of the object under test. In such applications, the same gain profile may be used at all locations on the scan path.

Alternatively, the gain profile may be selected from a group of gain profiles dependent upon the position on the scan path.

The gain profiles may be selected automatically with reference to a simulated ultrasound response.

The gain profiles may be selected automatically with reference to a measured ultrasound response.

The gain profiles may be selected through user interaction with the ultrasound system.

FIG. 1 is a block diagram of an exemplary ultrasound system 100 in accordance with some embodiments of the invention. In operation, a pulse of ultrasound generated from a first ultrasonic transducer (T1) 102 is reflected from or transmitted through an object to be imaged or otherwise tested. Reflected ultrasound may be sensed by the first transducer 102 in a pulse echo system, or by a second transducer (T2) 104. In a through transmission scan, transmitted sound is sensed by the second transducer 104. A control module 106 of a computer 108 controls a waveform generator 110 to generate a digital waveform that is converted to an analog waveform by a digital-to-analog converter (DAC) 112. A driver 114 amplifies the analog signal. Transmitted and/or reflected ultrasound is sensed by the transducers 102 and 104. A transmit/receive (T/R) switch 116 is used to select whether the amplified signal is coupled to the transducer 102, or whether the signal generated by the transducer 102 in response to sensed ultrasound is passed to low-noise pre-amplifier 118. The pre-amplified sensed signals are passed to a level adjuster 120, filter 122, and then to analog to digital converter (ADC) 124. In one embodiment, the digitized samples are stored in a memory 126 of the computer 108 and may be processed by processor 134. In a further embodiment, the digitized samples are stored in a memory of the ADC 124. A selected subset of the samples may be transferred to the memory 126 of the computer 108 or sent to a display unit. The control module 106 synchronizes the timing to the various components of the system, including the DAC 112, the T/R switch 116, the level adjuster 120, and the ADC 124. In particular, the gain or attenuation of the level adjuster 120 is varied dependent upon the time since the ultrasonic pulse was generated or the time since the initial response (from the front surface of the part in a pulse echo system, for example) is detected.

The gain of the level adjuster 120 is adjusted dynamically by a gain profile generator 136. The gain profile generator 136 retrieves a gain profile description from the memory 126, as directed by the user interface 128, and derives a gain profile from the description. In operation, the gain profile is applied to the level adjuster 120 under timing control of the control module 106.

A display 130 may be used to display graphical waveforms, a graphical user interface and other information, under the control of a display processor 132.

The level adjuster 120 may be a variable gain amplifier, a variable attenuator, a multiplying digital to analog converter or a combination thereof.

In a further embodiment, the level adjuster 120 is implemented in software and is applied to the digitized samples rather than the analog transducer signal. In this embodiment, the level adjuster is implemented after the ADC 124. The software, which may be executed in the processor of computer 108 for example, operates to multiply the digitized sample values by discrete gain values. An advantage of this approach is that the gain profile may be adjusted dependent upon the recorded signal. A further advantage is a reduction in the cost and complexity of the hardware.

In a still further embodiment, a combination of analog and digital level adjustment is used.

Multiple sensing transducers may be used, in which case the signal path comprising elements, 118, 120, 122 and 124 may be duplicated for each additional transducer.

Multiple transmitting transducers may be used, in which the signal path comprising elements, 110, 112 and 114 may be duplicated for each additional transducer.

The amplitude of the wave generated by an ultrasound element in the transducer 102 decreases as the wave propagates through the object under test. The amplitude tends to decrease as the wave is reflected, transmitted, scattered and absorbed by the object being imaged, and as the wave spreads geometrically. Generally, the longer the propagation time from the transmitting transducer to the receiving transducer, the greater the reduction in signal amplitude.

In systems where the ultrasound is generated at very high frequencies (hundreds of megahertz or higher), the dynamic range and resolution of the ADC 124 are limited. As a result, the digitized signals do not exactly match the analog signals. The error due to finite resolution is termed quantization noise. Quantization noise is largely independent of the signal level, so it is advantageous to have larger signals entering the ADC. However, the fixed gain of the pre-amplifier 118 is constrained because of the finite dynamic range of the ADC.

One approach is to use non-linear compression of the signals to boost low level signals relative to high level signals.

A further approach is to increase the gain of the level adjuster over time as the signal level decreases. Variable gain amplifiers have been used successfully in medical ultrasound. In that application, an image is captured using arrays of transmitting and receiving transducers together with phased-array beamforming. The structure of the objects being scanned is complicated and three-dimensional, so the gain of the variable gain amplifiers is generally increased with time in simple linear or exponential manner with a decay set by an operator.

In contrast, the structure of many electronic components is substantially laminar, since components may be constructed in layers, or multiple silicon dies may be stacked, one on top of the other. Molded flip chips also tend to have a laminar structure.

Electronic components may be imaged by moving a transducer across the component in a scan path and generating ultrasonic pulses at a number of different positions. The scan path is often substantially parallel to the laminar structure of the component.

In accordance with one aspect of the invention, it is recognized that the level adjustment of the level adjuster may be selected in accordance with the general structure of the object being imaged.

This approach is particularly useful when a number of components having the same general structure are to be imaged.

In the sequel, we refer to the variable gain of the level adjuster, but it is to be recognized that the 'gain' may be less than unity, since at a given time the level adjuster may attenuate the signal or amplify it.

In one embodiment, the time waveform of the response signal is determined by simulating the acoustic response of the object to be imaged.

In a further embodiment, the time waveform of the response signal is measured during a calibration phase.

Figure 2:
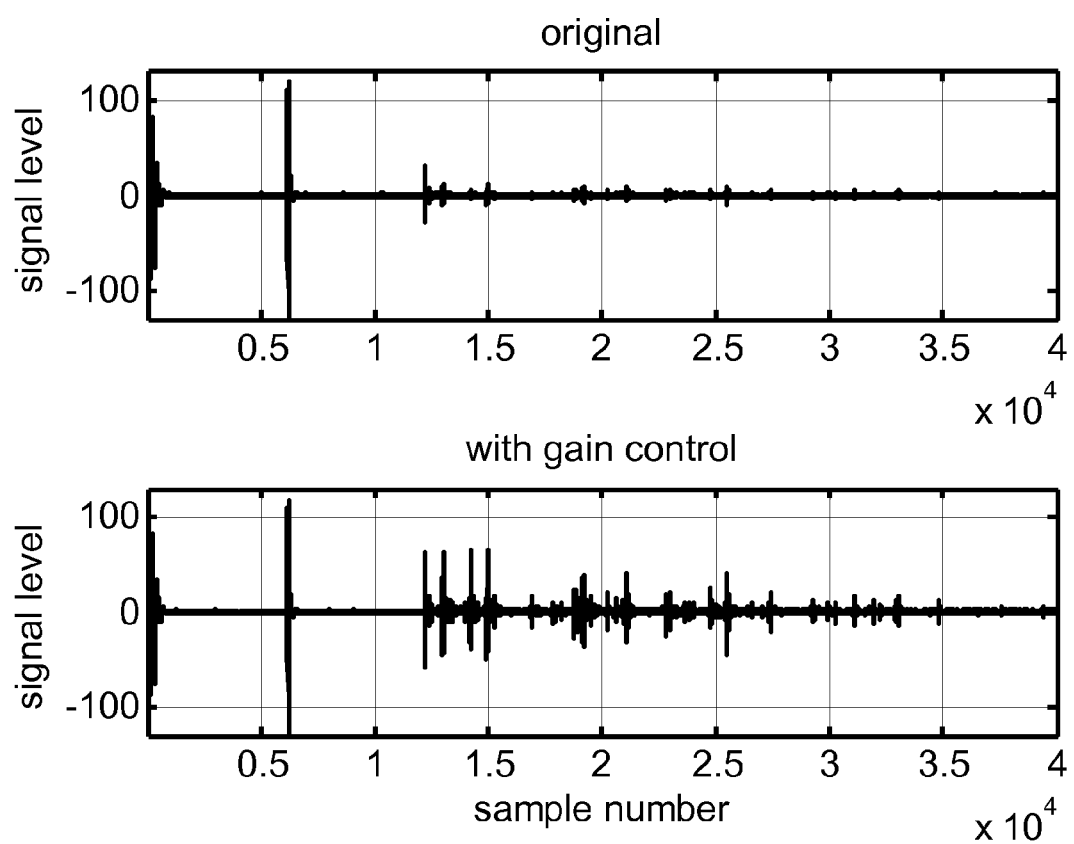
FIG. 2 shows graphs of an exemplary response signal, with and without dynamic level adjustment, from an object excited by an ultrasound pulse in accordance with some embodiments of the invention.

The time waveform, or profile, of the variable gain may be determined automatically from the simulated response or the measured response, or a combination thereof. In one embodiment, the time waveform, or profile, of the variable gain is selected by user interaction with the computer 108 in FIG. 1, via a user interface 128, in response to a display of the response on the display unit 130. In one embodiment, the display unit 130 is driven by the display processor 132 of the computer 108 and displays the time waveform of the response (also called the A-scan). FIG. 2 shows time waveforms of reflections (echoes) from an object excited by an ultrasound pulse. The upper plot in FIG. 2 shows the case where the level adjuster has a gain that does not vary over time. Generally, successive reflections have smaller amplitudes. The lower plot in FIG. 2 shows the case where the level adjuster has a gain that is altered over time. The gain profile may have a generally increasing trend, but may increase or decrease in any given time period. This is because the strength of the reflection depends upon the degree of impedance mismatch and the strength of the exciting signal. The later reflections in the lower plot are larger than the corresponding reflections in the upper plot. However, the noise level in both plots is substantially the same. This is because most of the noise is quantization noise that is added after the variable gain has been applied. Thus, the signal-to-noise ratio is greater for the signal in the lower plot, which has been modified by a time dependent variable gain. Improved signal-to noise ratio generally results in a higher quality image. The waveforms in FIG. 2 were measured by a scanning acoustic microscope operating in the 10-200 megahertz range, but higher frequencies may be used.

Figure 3:
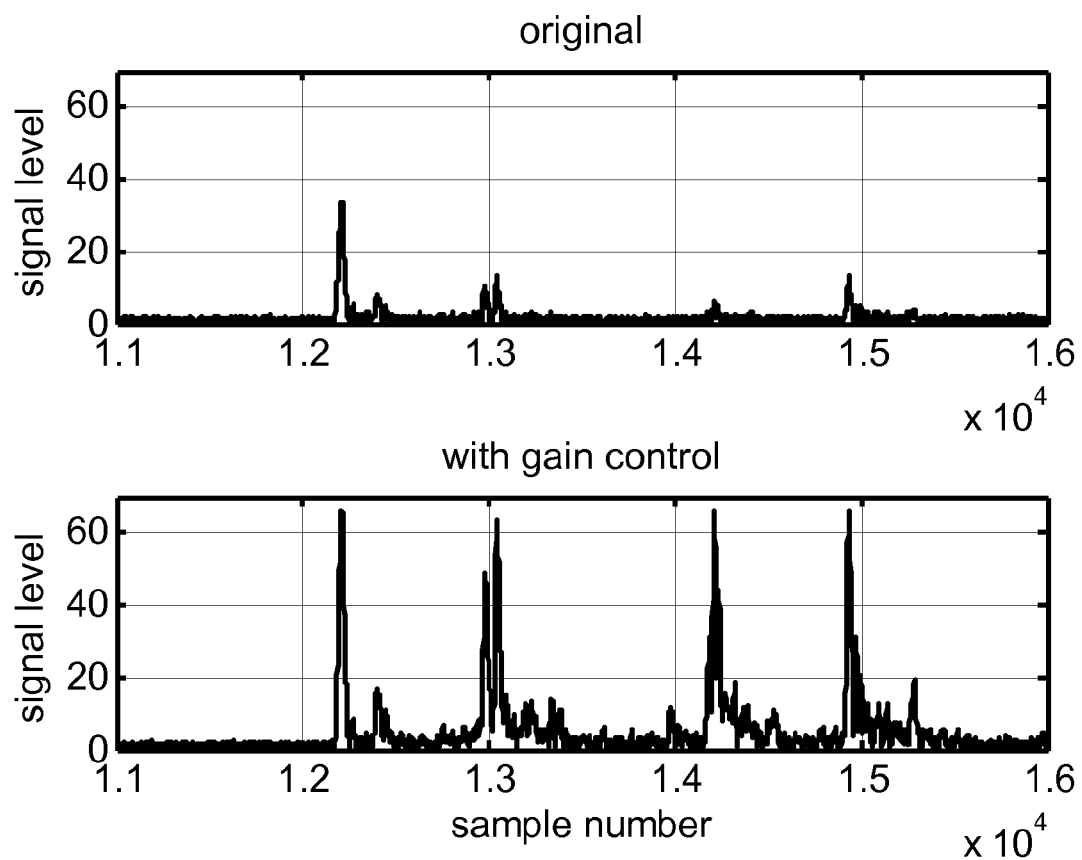
FIG. 3 shows the time envelopes of various sections of the response signals shown in FIG. 2.

More detail is shown in FIG. 3, which shows the envelope of a corresponding section of the plots in FIG. 2. For example, the reflection just before sample number 14,000 is clearly visible in the lower plot, but is lost in the noise in the upper plot. This indicates a significant increase in signal-to-noise ratio and will result in a more accurate test.

Benefits of this increased signal-to-noise ratio include: (i) increased penetration of ultrasound with higher frequencies, (ii) better equalization of reflections from deeper stacked die interfaces, without saturating shallower ones, and (iii) better triggering, since the front surface reflection may be increased without saturating internal reflections.

Figure 4:
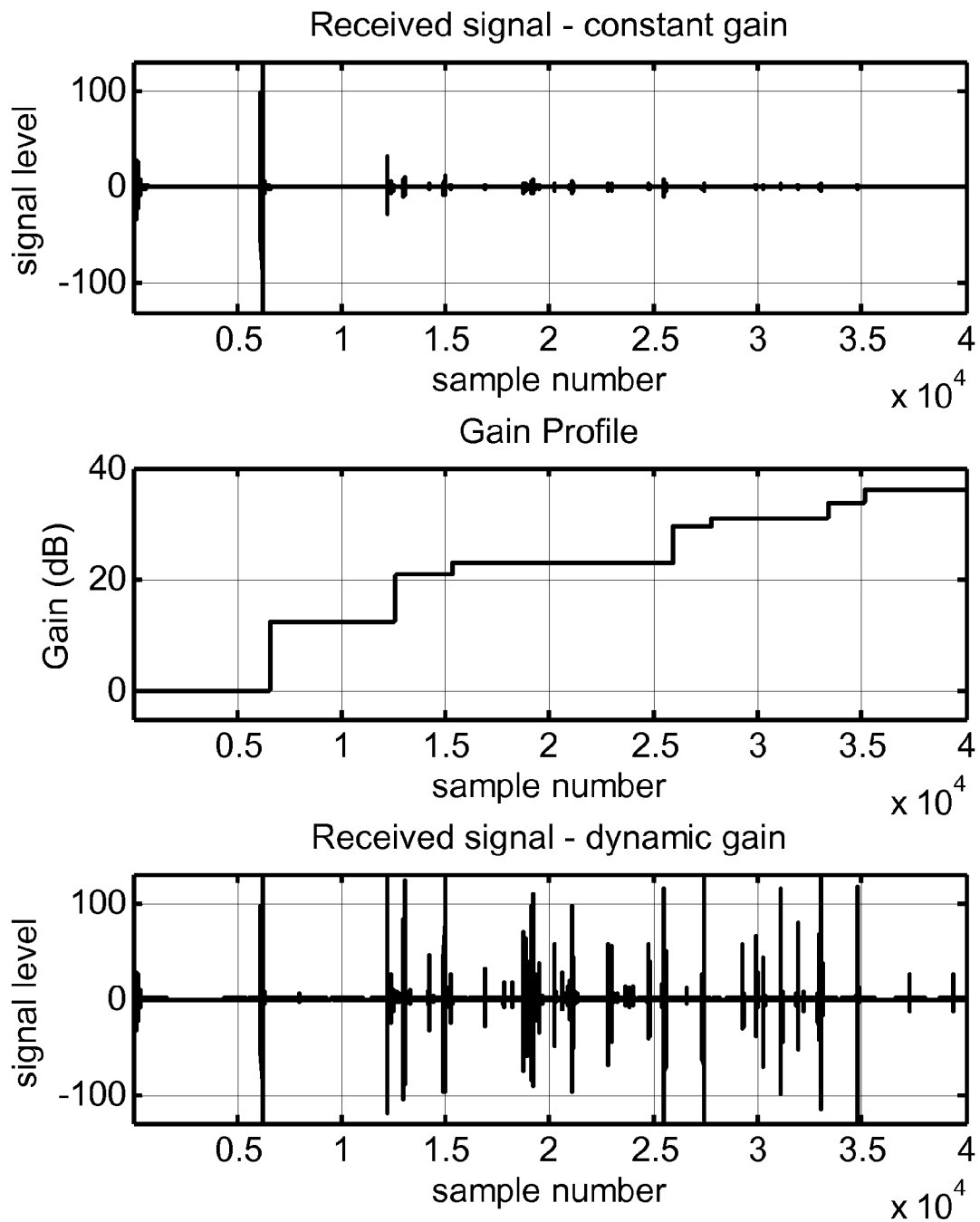
FIG. 4 shows graphs of an exemplary response signal with and without dynamic level adjustment, together with a graph of an exemplary gain profile, in accordance with some embodiments of the invention.

A further example is shown in FIG. 4. This plot shows a simulation of dynamic gain control. The upper plot in FIG. 4 shows the time waveform of the original received signal as a function of sample number (time). The middle plot shows time dependent gain, in decibels, applied by the level adjuster, and the lower plot shows the received waveform measured with the time dependent gain applied. This simulation shows the effect of gain control on the signal amplitudes. However, in the simulation, the gain was applied to the noise as well, so the noise levels in an actual measurement would be lower than shown. In this example, the gain increases monotonically, but this may not always be the case, since large impedance mismatches deep in an object may produce bigger responses than smaller impedance mismatches shallower in the object.

An exemplary embodiment of a Stacked Die Imaging (SDI) system for ultrasonic scanning of stacked die is described in the sequel with reference to FIGS. 5-8. To a standard scanning acoustic microscope, the SDI package adds (1) a level adjuster circuit that is used to equalize the reflections based on a user-created set of gain values (variable gain profile) and (2) a user interface to create the gain profile to be applied in order to equalize the reflections. In this embodiment, operator interaction via a user interface is used to set the gain values.

Figure 5:
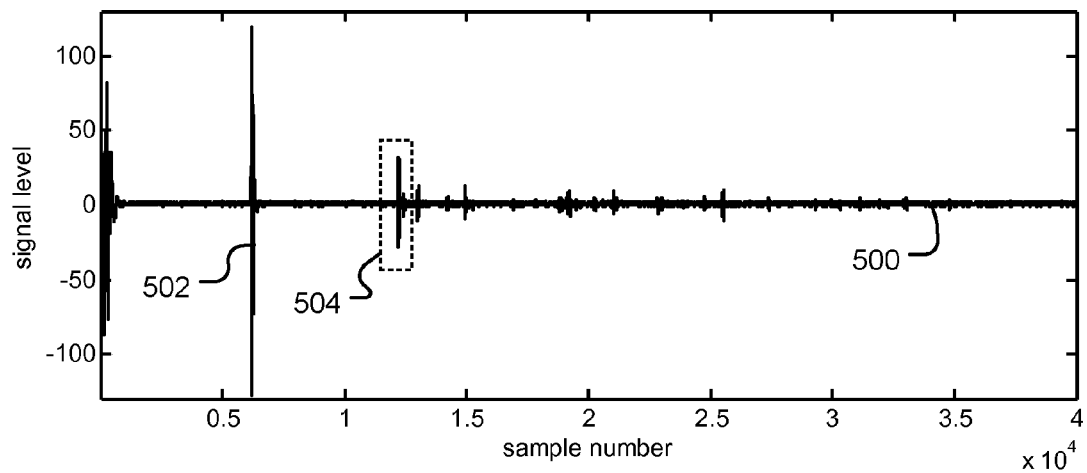
FIG. 5 shows part of a graphical user interface, displaying a response signal, in accordance with some embodiments of the invention.

FIG. 5 is a display of an exemplary time waveform 500 received from a transducer. The waveform 500 is displayed to the user. In this example, the high level return 502 corresponds to a reflection of the ultrasonic pulse from the surface of the part being scanned that is closest to the transducer (called the 'front' surface in the sequel). Via a user interface device, such as a computer mouse or a keyboard, the user selects a region 504 of the waveform. The region 504 corresponds to a time period or time gate in which a refection from an interior feature of the part is sensed by the transducer. This selection determines the time window for which the user wants to set a gain value.

Figure 6:
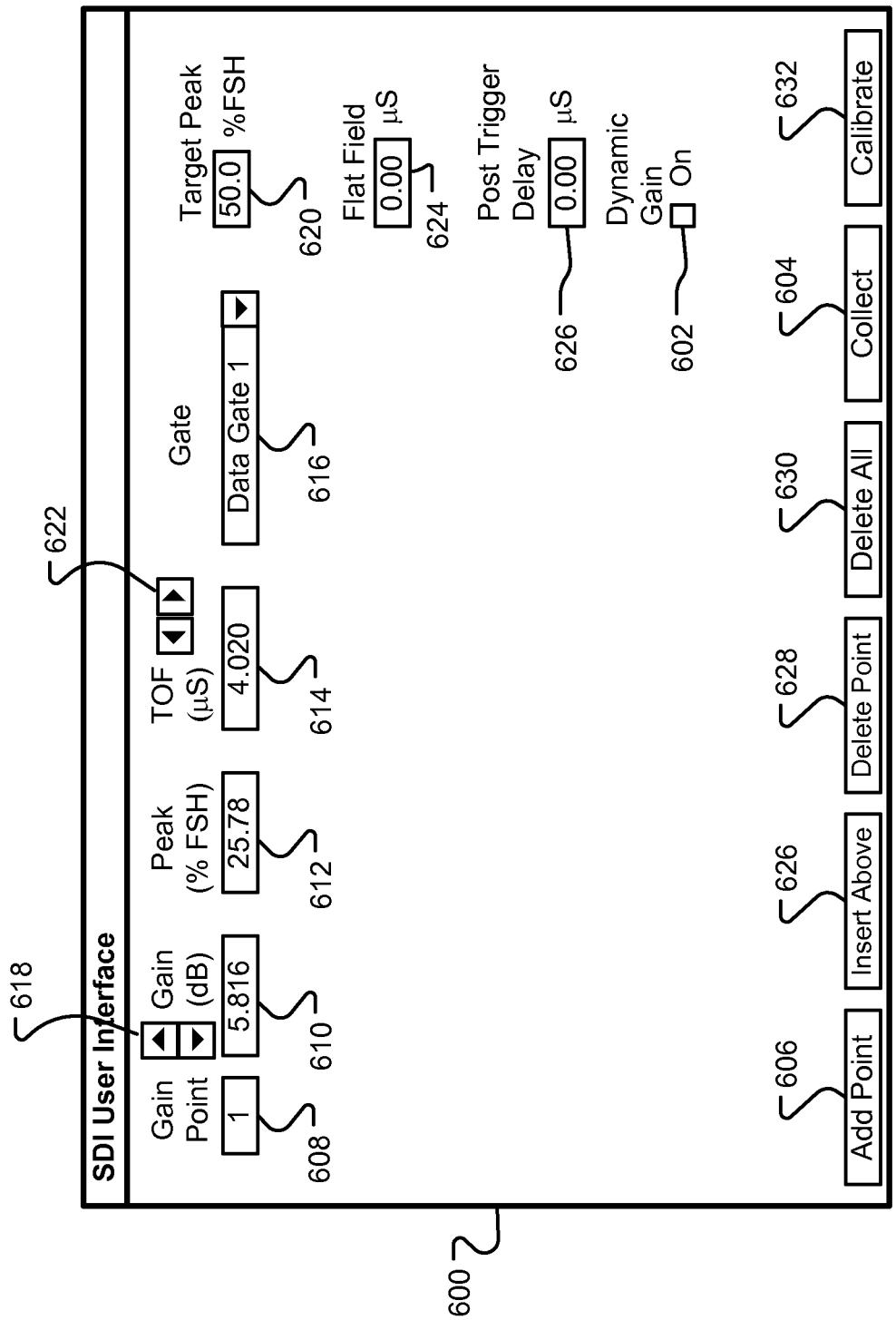
FIG. 6 shows a screen view of an exemplary data entry form that is part of a user interface in accordance with some embodiments of the present invention.

FIG. 6 is a representation of an exemplary user interface for setting a gain profile. This interface may be displayed on the same screen as the waveform display shown in FIG. 5, and may be activated or deactivated by the user. In this embodiment, a number of points on a gain profile are entered by user interaction with a data entry form. In an alternate embodiment, the gain profile is set by user interaction with a graphically displayed gain curve that a user simply moves up or down at a chosen time value (using a 'click and drag' technique for example) to achieve the equalization desired.

The exemplary interface in FIG. 6 comprises a screen view, or window, 600. A check box 602 controls whether dynamic gain is active or not when a new waveform is collected. The peak amplitude and time of flight values of the gate region displayed in box 616 are collected by activating button 604. This refreshes the values shown in edit boxes 612 and 614, respectively. A control button 606 may be activated to cause a new line of form elements 608, 610, 612, 614 and 616 to be displayed. The form elements allow gain parameters to be entered by the user. Element 608 displays an identifier or index, such as the line number of the data entry form.

Edit box 614 displays the time of flight (TOF) corresponding to the time between the reflection (502 and FIG. 5) from the front surface of the object under inspection and the reflection for which gain adjustment is being made. The time of flight may be selected graphically, by manipulating the window 504 in FIG. 5, or it may be selected by typing into the edit box 614, or it may be selected by using the increment and decrement controls 622. In the latter cases, the window in FIG. 5 may be adjusted to correspond to the user-modified value.

Box 612 displays the level of the reflection (the peak of the waveform in window 504 in FIG. 5) as a percentage of full scale.

The gain to be applied to the selected reflection may be selected by typing into edit box 610, or by adjusting the level in the box using increment and decrement controls 618. Alternatively, a percentage level may be entered into the Target Peak edit box 620. When the calibrate button 632 is activated, the gain in box 610 is set automatically such that, when the gain applied, the peak value of the resulting reflection matches the target percentage of full scale input. The calculated gain is displayed in edit box 610.

List box 616 allows the user to select which data gate is to be used for the selected reflection. The data gate is selected from a menu of data gates.

The information entered in boxes 610 and 614 of this line of the data entry form is used to set one point of the gain profile for the level adjuster.

A new line, corresponding to a new gain point, may be added to the data entry form by activating button 606. This adds a new line below the existing lines. Alternatively, button 626 may be activated to add a new form line above a current form line.

The existing form line may be deleted by activating button 628. This removes the corresponding gain point from the gain profile.

All of the existing form lines may be deleted by activating button 630. This removes all of the gain points from the gain profile.

In one embodiment, button 632 may be activated to set the gain displayed in edit box 610 automatically. In a further embodiment, multiple peaks in the A-scan waveform are found and the gain profile is set to adjust these peaks, or an envelope of the peaks, to a predetermined level or as close to the level as possible subject to constraints such as a maximum gain level.

Figure 7:
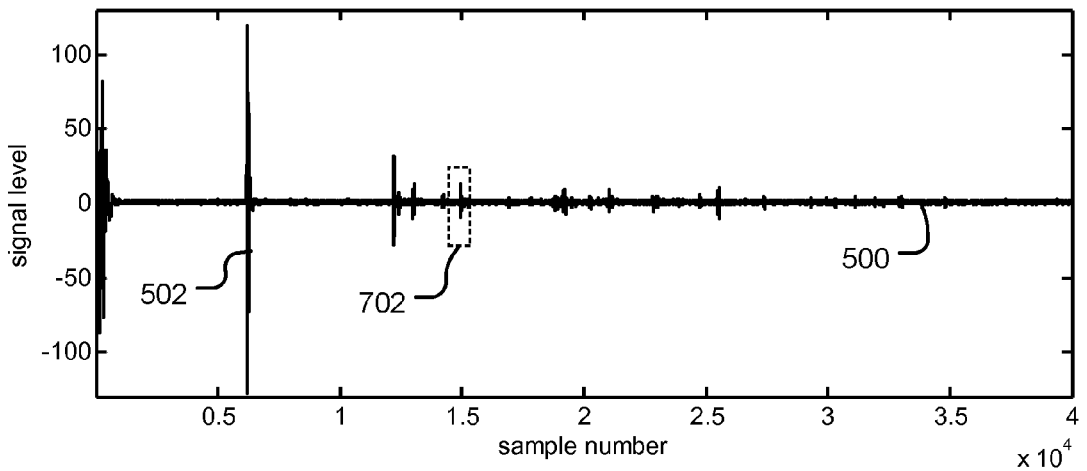
FIG. 7 shows part of a graphical user interface, displaying a response signal, in accordance with some embodiments of the invention.

FIG. 7 is a further display of the received time waveform 500 from a transducer. In this view the user has selected a region 702 of the waveform. The region 702 corresponds to a time period in which a refection from an interior feature of the part is sensed by the transducer. This selection determines the next time window for which the user wants to set a gain value.

Figure 8:
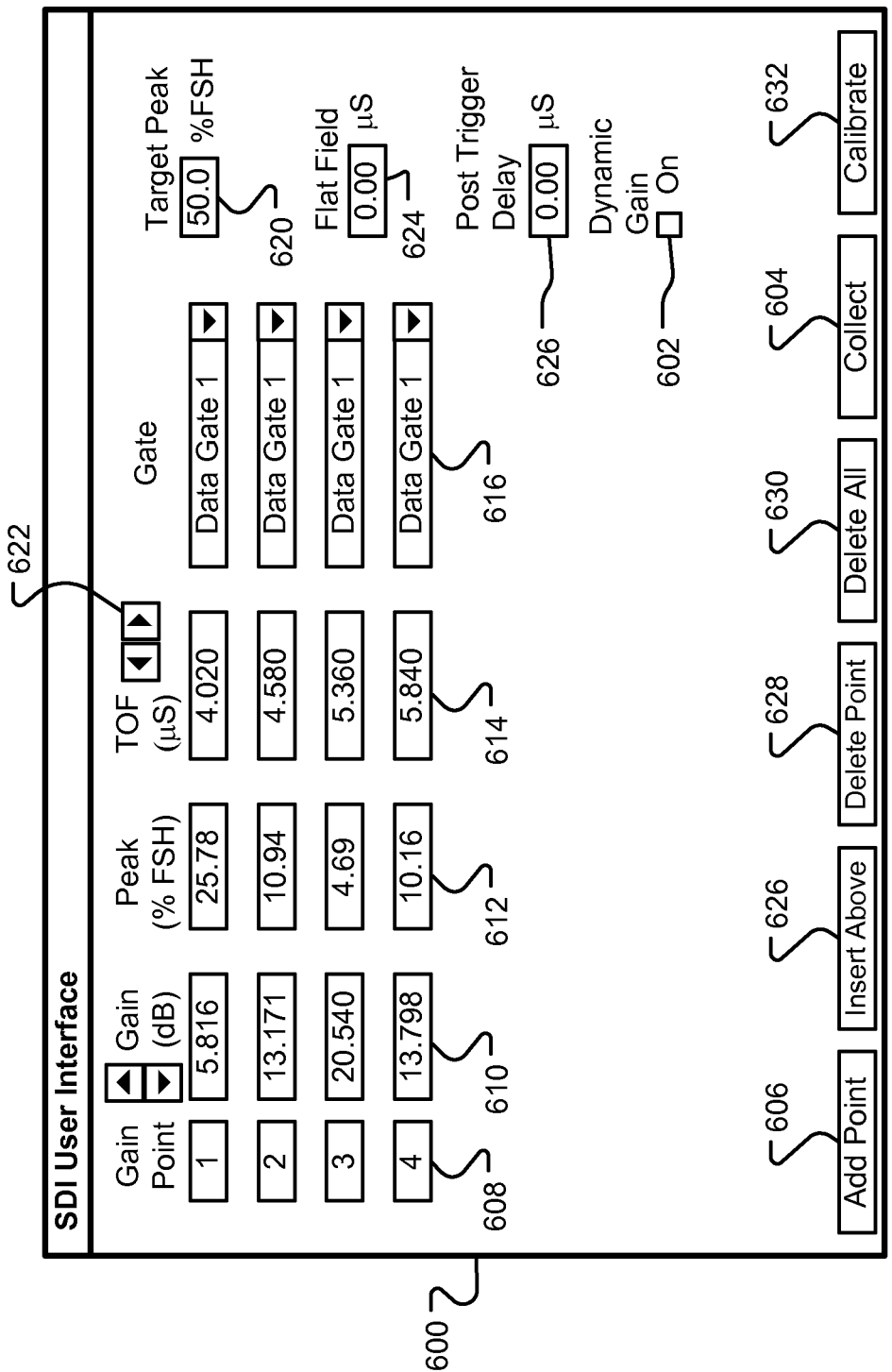
FIG. 8 shows a further screen view of an exemplary data entry form that is part of a user interface in accordance with some embodiments of the present invention.

FIG. 8 is a further representation of an exemplary user interface displayed to the user. In FIG. 8, four lines of the data entry form have been completed, defining four points or regions of the gain profile. The time of flight and the peak value of the selected reflection (shown in FIG. 7) are displayed in boxes 614 and 612, respectively. Each new point has an identifier in box 608. In FIG. 8, four points have been set. The gain profile is specified, at least in part, by the gain values in boxes 610 and the time values in boxes 614.

Figure 9:
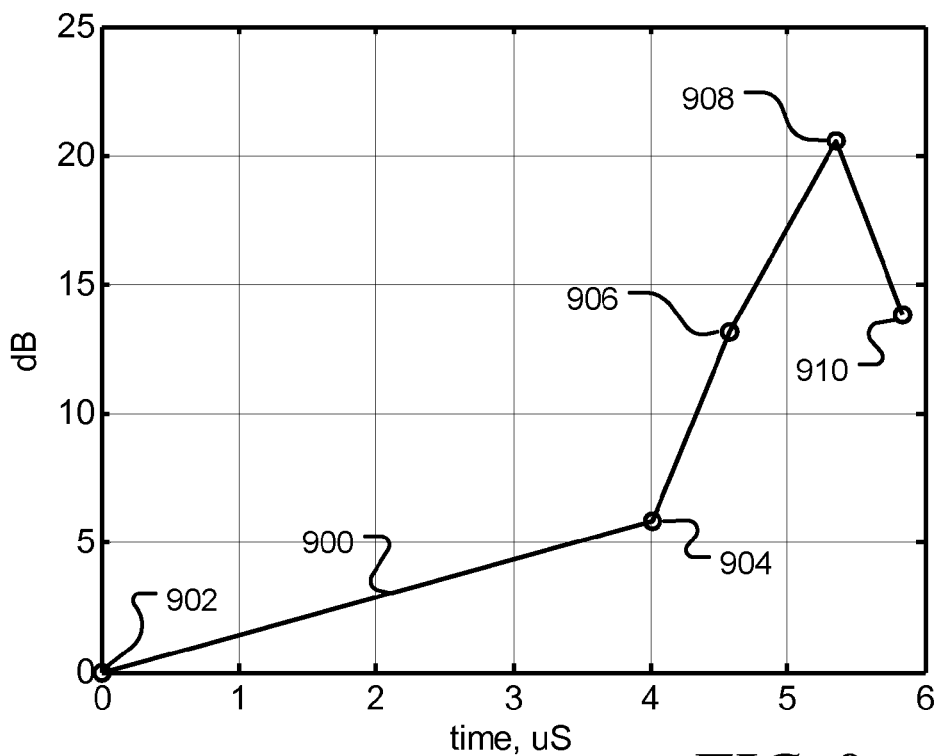
FIG. 9 is a graph of an exemplary gain profile, plotted as a function of time, in accordance with some embodiments of the invention.

The complete data entry form defines the gain values at discrete times. The gain profile may be calculated by interpolating between the points set in the data entry form to obtain the gain values at other times, such as a set of uniformly spaced times. An example using linear interpolation is shown in FIG. 9. FIG. 9 shows the gain profile 900 as a function of the time of flight. This defines the gain to be applied by the level adjuster. The initial gain is set to unity (0 dB) at point 902. Points 902, 904, 906 and 908 correspond to stored gain points at stored time values, as defined in the data entry form in FIG. 8. In one embodiment, a gain profile is determined from the selected description of a gain profile by selecting a set of time values and interpolating the stored gain values from the stored time values to intermediate time values. In this embodiment, intermediate gain values are found by linear interpolation, but the intermediate points may be found by other means. For example, the gain profile shown in FIG. 10 uses cubic interpolation between the specified gain points, and the gain profile shown in the middle plot of FIG. 4 shows a further gain profile having extended regions of constant gain. In general, the gain profile is dependent upon the internal structure of the object to be tested and need not be monotonically increasing.

Figure 10:
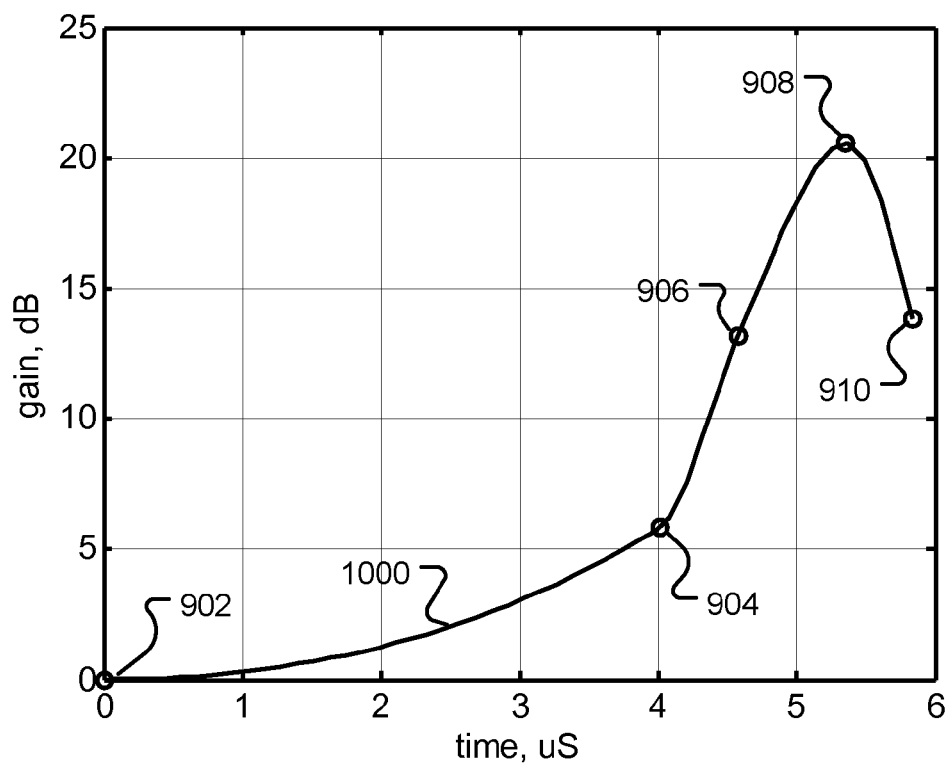
FIG. 10 is a graph of a further exemplary gain profile, plotted as a function of time, in accordance with some embodiments of the invention.

In a further embodiment, the user may interact with a displayed gain profile, such as those shown in FIG. 9 and FIG. 10, by graphically selecting a point on the graph and dragging it to a desired gain setting. A near simultaneous display of the resulting A-scan waveform (predicted or measured) may be used to display the effect of the modified gain profile.

Once created, the gain settings are stored along with the other scan settings in a parameter file or recipe in the computer memory. The gains may be stored as a lookup table that is triggered by the detection of a reflection and read out to a digital output that is used to control the level adjuster.

The gain profile need only be specified once for a particular type of part to be inspected. In operation, a user can simply load the profile for the appropriate part and perform an inspection of one or more parts of the same type.

Figure 11:
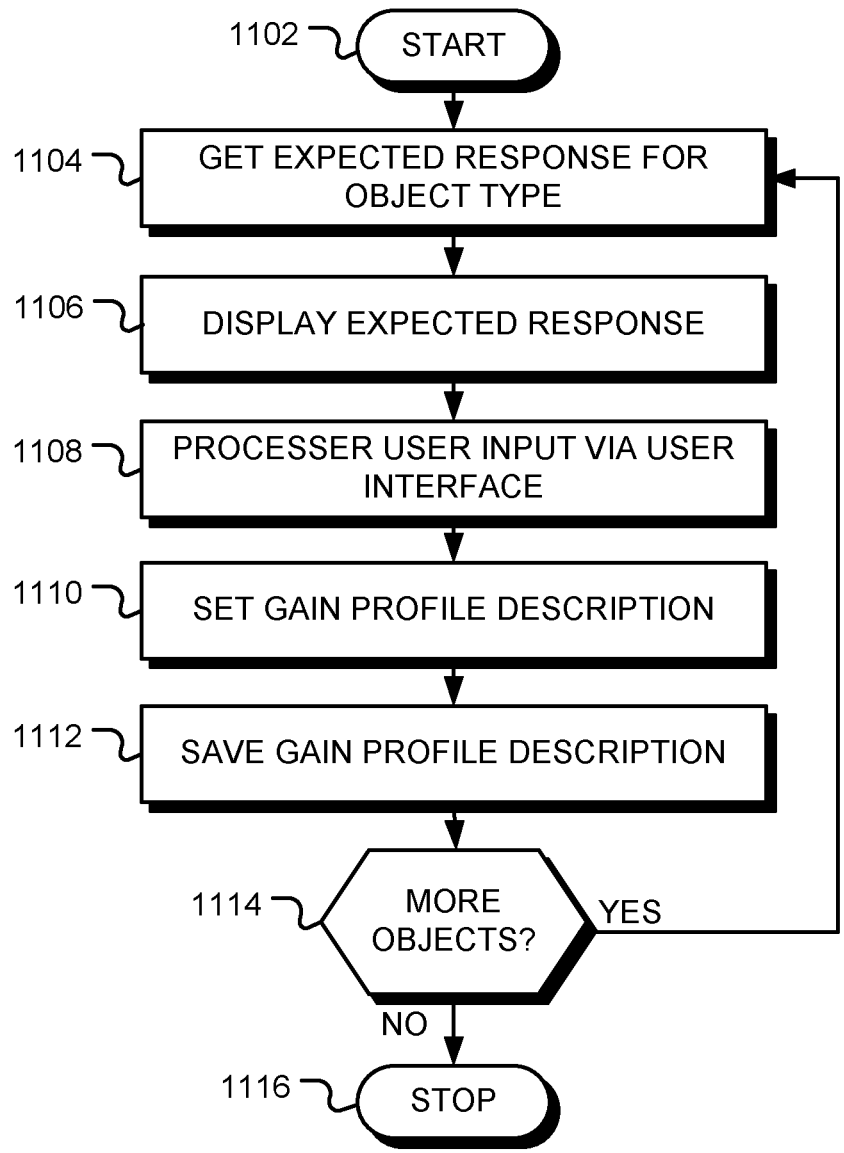
FIG. 11 is a flow chart of an exemplary calibration phase method in accordance with some embodiments of the invention.

One embodiment of the invention relates to a method for dynamically adjusting the level of a response signal from an ultrasound transducer. The method includes a calibration phase and a measurement phase. FIG. 11 is a flow chart an exemplary calibration phase method. Following start block 1102 in FIG. 11, an expected response for the type of object under consideration is retrieved at block 1104. In one embodiment, the expected response comprises a response signal computed using simulation of the type of object to be tested. A method of simulation is disclosed in co-pending patent application Ser. No. 11/482,347, filed Jul. 7, 2006. In a further embodiment, the expected response comprises a previously measured response signal from the type of object to be tested. A description of the gain profile may be derived automatically from the expected response. Alternatively, as depicted in FIG. 11, a description of the gain profile may be determined by interaction with a user via a user interface. At block 1106, the expected response signal is displayed to the user. At block 1108, input from the user is processed and, at block 1110 a description of the gain profile is generated from the user input. For example, user input may be received via a graphical user interface and processed to select time values and corresponding gain values. The graphical user interface may comprise a data entry form for data entry or a graphical display of the gain profile to be adjusted by a 'click and drag' technique, for example. At block 1112, the description of the gain profile is saved in a memory for later recall. Multiple gain profiles may be stored in the memory and may be indexed by an identifier of the object type that is also stored in the memory.

The description of the gain profile may comprise a lookup table of gain values corresponding, for example, to the gain values at regular time intervals. Alternatively, the description of a gain profile comprises a set of time values and a corresponding set of gain values, from which the gain profile at other intermediate times can be derived by interpolation. In a further embodiment, the description comprises a set of parameters, such as polynomial coefficients, from which a gain profile may be derived.

If gain profile descriptions for other object types are to be generated and saved, as depicted by the positive branch from decision block 1114, flow returns to block 1104. Otherwise, as depicted by the negative branch from decision block 1114, the method terminates at block 1116.

Figure 12:
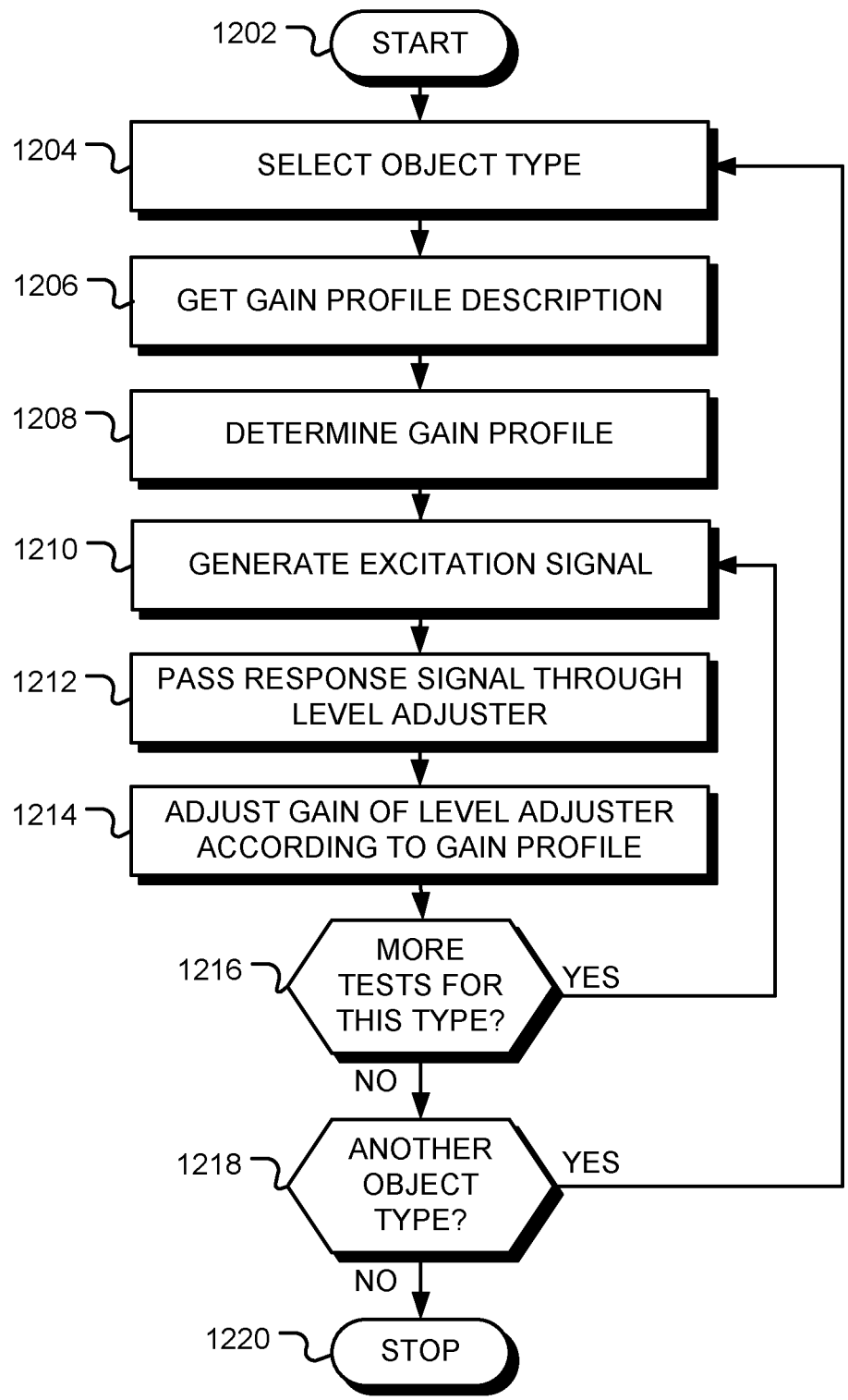
FIG. 12 is a flow chart of an exemplary measurement phase method in accordance with some embodiments of the invention.

FIG. 12 is a flow chart of an exemplary measurement phase method. Following start block 1202 in FIG. 12, the type of the object to be measured is selected at block 1204. This may be done by the user via a user interface, for example. At block 1206, the gain profile description for the selected object type is retrieved at block 1206. From this description, the actual gain profile is determined at block 1208. Testing of the object can then begin. At block 1210, an excitation signal is generated. This signal may drive an ultrasound transducer, for example. The response to the excitation produces a response signal. At block 1212, the response signal is passed through a level adjuster. At block 1214 the gain of the level adjuster is varied dynamically according to the gain profile as the signal passes through the level adjuster. The start of the application of the gain profile may be triggered at a prescribed time after the excitation signal is generated, or at a prescribed time after the first response from the object under test is detected in the response signal.

If more tests are to be performed on an object of the current type, as depicted by the positive branch from decision block 1216, flow returns to block 1210, otherwise flow continues to decision block 1218. For example, in a scanning acoustic microscope, an object is excited at multiple positions as a transducer is scanned across its surface. If the structure of the parts is substantially laminar, as is the case for stacked integrated circuits, the same gain profile may be used at difference locations on the parts.

In this manner, the benefits of dynamic level adjustment of the response signal are achieved with minimal user intervention once a description of a gain profile for part of the same type has been stored in the memory.

The gain profile may be determined at different physical location. Once a description of a gain profile is available for a particular part, the profile may be distributed to multiple different ultrasound systems via a computer readable medium or a communication network, for example.

An advantage of storing a gain profile description, rather than the gain profile, is that the gain profile may be generated for digitally controlled level adjusters at different data rates from the same description. However, the description may itself be a set of a gain values at one particular data rate.

Multiple objects, such as integrated circuits and MEMS, may be scanned together. If the objects are parts are of the same type, the same gain profile may be used. Thus, as depicted by the positive branch from decision block 1216, flow returns to block 1210 if another object of the same type is to be scanned—without the need to retrieve or set up a new gain profile. If no more objects of the same type are to be scanned, as depicted by the negative branch from decision block 1216, flow continues to decision block 1218. If more objects, of a different type, are to be scanned, as depicted by the positive branch from decision block 1218, flow returns to block 1204, otherwise the method terminates at block 1220.

In accordance with one embodiment, an apparatus for dynamic adjustment of the level of a response signal from an ultrasound transducer includes a memory that stores at least one gain profile description, a gain profile generator operable to generate a gain profile from a selected gain profile description of the at least one gain profile description; and a level adjuster responsive to the response signal, the level adjuster dynamically adjusting the level of the response signal in accordance with the gain profile to produce a level adjusted response signal. The memory may be used to store a plurality of gain profile descriptions, each corresponding to a type of object, the apparatus further comprising. A user interface displays a list of the object types to the user and receives information from the user; and a selector processes the user input to select the gain profile from the plurality of gain profile descriptions.

The gain profile may include one or more periods of increasing gain and one or more periods of decreasing gain.

The response signal is a sensed signal corresponding to an echo of an excitation pulse or corresponding to ultrasound pulse transmitted through an object in response to an excitation pulse.

Figure 13:
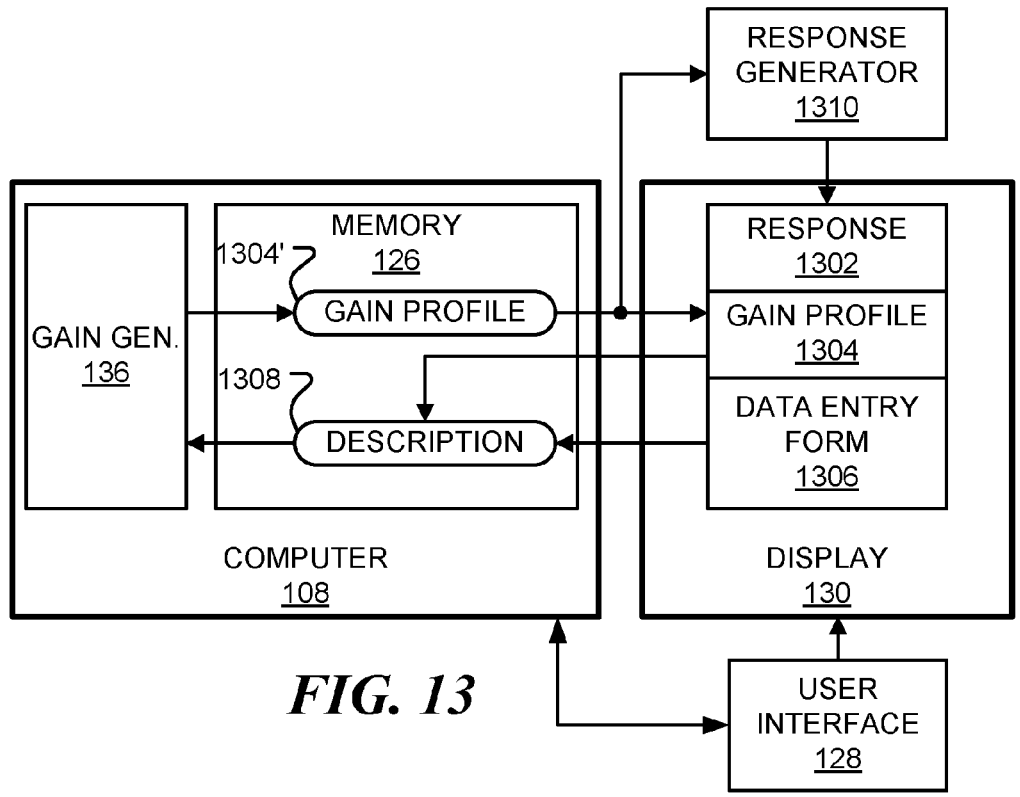
FIG. 13 is a block diagram of an apparatus for determining a gain profile description of an object to be tested, in accordance with certain embodiments of the invention.

FIG. 13 is a block diagram of an apparatus for determining a gain profile description of an object to be tested in accordance with certain embodiments of the invention. The apparatus comprises a display 130 that displays an expected response 1302, and a user interface that includes a gain profile graph 1304 and a data entry form 1306. The expected response generator may be a computer simulation of the object or a recorder of a prior response.

In operation, an operator interacts with the gain profile and/or the data entry form via a user interface 128. A computer or other processor 108 functions as a description generator that processes user data to generate a gain profile description 1308 that may be stored in a memory 126 of the computer 108. The display 130, user interface 128 and processor 134 operate together as a description generator that generates a gain profile description. The gain profile description is used by gain profile generator 136 to generate a gain profile for dynamic adjustment of the level of a response signal.

In one embodiment, the data entry form 1306 allows the user to input a plurality of time values and a plurality of gain values, associated with the plurality of time values, to describe the gain profile.

In a further embodiment, the user interacts with the graphical display of the gain profile 1304 to describe the gain profile.

In one embodiment, the expected response generator 1310 comprises a computer simulation of an object to be tested.

In a further embodiment, the expected response generator 1310 comprises a recorder of a prior response.

In accordance with one embodiment of the invention, an apparatus for dynamically adjusting the level of a response signal from an object under ultrasonic testing includes a user interface, a gain profile selector, a gain generator and a level adjuster. The gain profile selector is operable to select a gain profile description dependent upon user interaction with the user interface. The gain generator is operable to generate a gain profile from the gain profile description. The level adjuster is operable to adjust the level of the response signal dynamically in accordance with the gain profile. The level adjuster may include a multiplying digital to analog converter, for example.

The gain profile descriptions corresponding to different types of objects to be tested may be stored in a local memory or in a remote memory accessible via a network such as the Internet.

Figure 14:
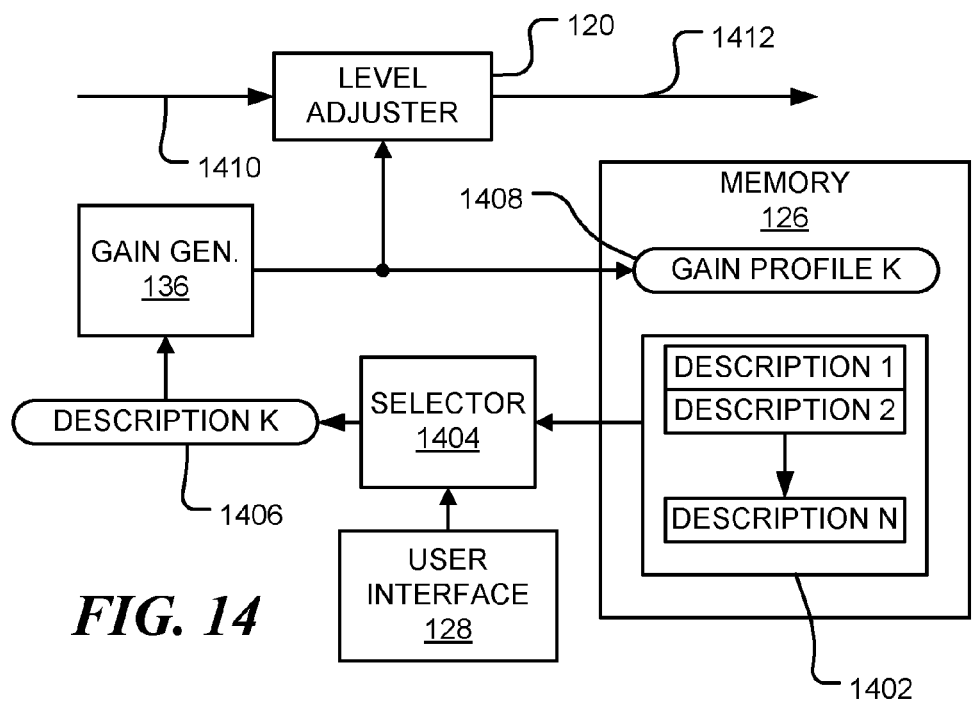
FIG. 14 is a block diagram of an apparatus for dynamic adjustment of the level of a response signal, in accordance with certain embodiments of the invention.

FIG. 14 is a block diagram of an apparatus for dynamic adjustment of the level of a response signal from an ultrasound transducer in accordance with certain embodiments of the invention. The apparatus comprises a memory 126 that stores one or more gain profile descriptions 1402 and a selector 1404. In operation, a user interface 128 displays a list of the object types to the user and receives information from the user. The selector 1404, which may be implemented in a processor, processes the user input and selects a gain profile description 1406 from the plurality of gain profile descriptions 1402. A gain profile generator 136 generates a gain profile 1408 from the selected gain profile description 1406. The gain profile 1408 may be stored in the memory 126 and/or passed to a level adjuster 120. The level adjuster 120 is responsive to a response signal 1410 and dynamically adjusts the level of the response signal 1410, in accordance with the gain profile 1408, to produce a level adjusted response signal 1412. The level adjusted signal may then be sampled and used to test the object that generated the response signal 1410.

Figure 15:
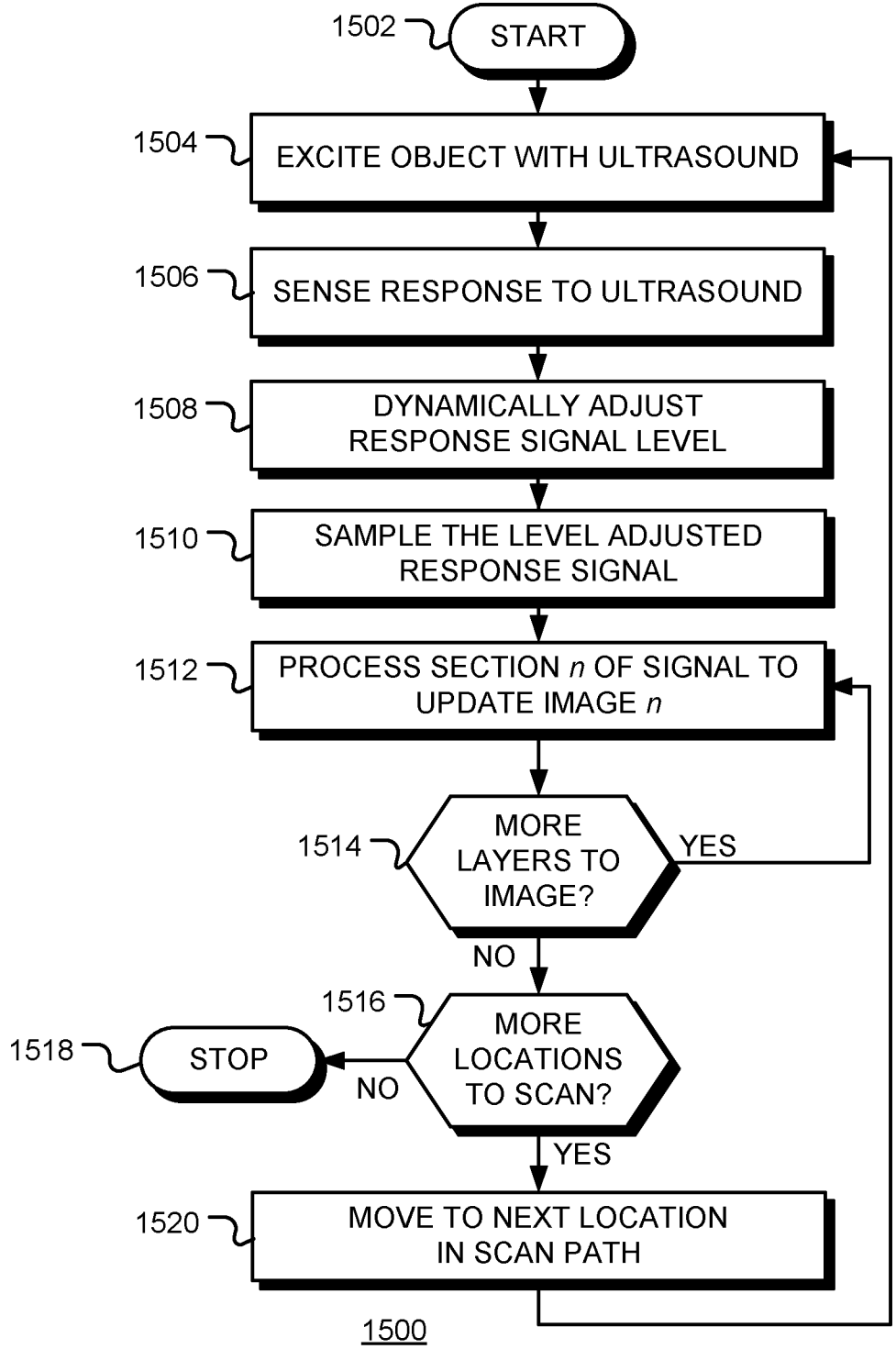
FIG. 15 is a flow chart of a method for ultrasonic imaging of a multi-layered object, in accordance with certain embodiments of the present invention.

FIG. 15 is a flow chart 1500 of a method for ultrasonic imaging of a multi-layered object in accordance with certain embodiments of the present invention. Following start block 1502, a multi-layered object is excited at block 1504 with a pulse of ultrasound at a first time. At block 1506 ultrasound produced by the multi-layered object in response to the pulse of ultrasound is sensed to obtain a response signal. At block 1508, during a time interval corresponding to the expected time of flight of ultrasound reflected from a layer of the multi-layered object, the level of the response signal is adjusted dynamically in accordance with a gain profile, to obtain a level adjusted response signal. This section or time interval of the response signal corresponds to a reflection from a layer of the multilayered object. At block 1510, the level adjusted response signal is sampled to obtain a sampled response signal and, at block 1512, the sampled response signal is processed to obtain an update to an ultrasound image of the layer of the multi-layered object. The section of the response signal in the $n^{th}$ time interval of each pulse is processed to update the $n^{th}$ image, to enable multiple images to be formed form a single scan.

If an additional layer of the multilayered object is to be imaged from the same ultrasound pulse, as depicted by the positive branch from decision block 1514, flow returns to block 1512. In this way, images of multiple layers may be obtained from a single ultrasound scan. For each pulse of ultrasound in a single scan multiple sections of the level adjusted response signal are identified, corresponding to reflections of ultrasound from a multiple layers of the multi-layered object. For each section n of the level adjusted response signal, the level adjusted response signal in that section is processed to update the $n^{th}$ image of the plurality of images. The update may comprise, for example, calculating an additional pixel value in a digital image from the level of the level adjusted response signal.

Once all sections of the level adjusted response signal have been processed, as depicted by the negative branch from decision block 1514, the process continues to decision block 1516. If all points in the scan path have been measured, as determined by the negative branch from decision block 1516, the process terminates at block 1518, otherwise flow continues to block 1520 and the position of the ultrasound excitation is changed. Flow then returns to block 1504 and the cycle is repeated for each position in the scan path.

The gain profile may be selected to equalize sections of the level adjusted response signal corresponding to reflections of ultrasound from layers of the multi-layered object.

It will be appreciated that embodiments of the invention described herein may comprise one or more conventional processors and unique stored program instructions that control the one or more processors to implement, in conjunction with certain non-processor circuits, some, most, or all of the functions of dynamic level adjustment described herein. The non-processor circuits may include, but are not limited to signal conditioning circuits, signal drivers, clock circuits, power source circuits, and user input devices. As such, these functions may be interpreted as a method to perform dynamic level adjustment. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

It will be appreciated that any module or component disclosed herein that executes instructions may include or otherwise have access to non-transient and tangible computer readable media or medium such as storage media, computer storage media, or data storage devices (removable or non-removable) such as, for example, magnetic disks, optical disks, or tape data storage. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the server, any component of or related to the network, backend, etc., or accessible or connectable thereto. Any application or module herein described may be implemented using computer readable/executable instructions that may be stored or otherwise held by such computer readable media.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method for dynamically adjusting a level of a response signal from an ultrasound transducer, the method comprising:
    in a measurement phase for an object under test:
        selecting a description of a gain profile in accordance with the object under test from one or more gain profile descriptions;
        determining the gain profile from the selected description of a gain profile,
        the gain profile defining the gain of a level adjuster as a function of time;
        passing the response signal from the object under test through the level adjuster; and
        dynamically adjusting the level of the response signal under timing control in accordance with the gain profile.

2. A method in accordance with claim 1, further comprising:
    in a calibration phase:
        setting the description of the gain profile dependent upon an expected response signal for an object to be tested; and
        storing the description of the gain profile.

3. A method in accordance with claim 2, wherein setting the description of a gain profile of the level adjuster dependent upon an expected response signal for the object to be tested comprises:
    displaying the expected response signal to a user; and
    processing user input via a graphical user interface to select time values and corresponding gain values that describe the gain profile.

4. A method in accordance with claim 3, wherein the graphical user interface comprises a data entry form.

5. A method in accordance with claim 3, wherein the graphical user interface comprises a graphical display of the gain profile.

6. A method in accordance with claim 2, wherein the expected response signal comprises a response signal computed using simulation of the object to be tested.

7. A method in accordance with claim 2, wherein the expected response signal comprises a previously measured response signal of the object to be tested.

8. A method in accordance with claim 2, wherein storing the description of the gain profile in a memory comprises storing a lookup table of gain values in the memory.

9. A method in accordance with claim 2, wherein storing the description of the gain profile in a memory comprises storing an identifier of the object to be tested.

10. A method in accordance with claim 2, wherein the description of a gain profile comprises a set of time values and a set of gain values, each gain value of the set of gain values corresponding to a time value of the set of time values.

11. A method in accordance with claim 2, wherein setting the description of a gain profile of a level adjuster comprises:
    identifying times of flight of a plurality of reflection components in the expected response signal, and
    for each time of flight of the plurality of reflection components, selecting a gain value such that after level adjustment the plurality of reflection components have approximately equal amplitude.

12. A method in accordance with claim 11, wherein setting the description of a gain profile is dependent upon at least one constraint on the gain profile.

13. A method in accordance with claim 1, wherein determining a gain profile from the selected description of a gain profile comprises:
    selecting a set of time values; and
    interpolating the stored gain values from the stored time values to the selected set of time values.

14. A method in accordance with claim 1, wherein the object under test comprises a plurality of layers.

15. A method in accordance with claim 1, further comprising receiving the one or more gain profile descriptions via a network.

16. A method in accordance with claim 1, further comprising reading the one or more gain profile descriptions from a computer readable medium.

17. A method in accordance with claim 1, further comprising sampling the response signal to obtain a sampled response signal, wherein adjusting the level of the response signal is performed before the response signal is sampled.

18. A method in accordance with claim 1, further comprising sampling the response signal to obtain a sampled response signal, wherein adjusting the level of the response signal is performed after the response signal is sampled.

19. An apparatus for determining a description of a gain profile for dynamic adjustment of a level of a response signal from an ultrasound receiver, the apparatus comprising:
    an expected response generator operable to generate an expected response signal expected to result from excitation of an object to be tested;

a description generator operable to generate a gain profile description to be used to generate a gain profile for dynamic adjustment of the level of the response signal; and a memory operable to store the gain profile description, where the expected response generator comprises an excitation waveform generator operable to supply an excitation waveform to an ultrasound transmitter that couples ultrasound to an object of the same type as the object to be tested, and where the expected response generator is operable to measure a response signal from the object of the same type as the object to be tested.

20. An apparatus in accordance with claim 19, wherein the description generator comprises:
a display operable to display the expected response;
a user interface; and
a processor operable to process user input to obtain the gain profile description.

21. An apparatus in accordance with claim 20, wherein the user interface comprises a form and wherein the user input comprises a plurality of time values and a plurality of gain values associated with the plurality of time values.

22. An apparatus in accordance with claim 20, wherein the user interface comprises an interactive graphical display of the gain profile.

23. An apparatus in accordance with claim 19, wherein the expected response generator comprises a recorder of a prior response.

24. An apparatus in accordance with claim 19, where the expected response generator further comprises a computer simulation of a response, to an ultrasound excitation, of the object of the same type as the object to be tested.

25. An apparatus for determining a description of a gain profile for dynamic adjustment of a level of a response signal from an ultrasound transducer, the apparatus comprising:
an expected response generator operable to generate an expected response signal expected to result from excitation of an object under test;
a description generator operable to generate a gain profile description to be used to generate a gain profile for dynamic adjustment of the level of the response signal; and
a memory operable to store the gain profile description,
wherein the expected response generator comprises a computer simulation of a response of the object to an ultrasound excitation.

26. An apparatus in accordance with claim 25, wherein the object under test comprises a multi-layered object, and wherein the computer simulation provides estimated responses from signal paths that include multiple internal reflections in the multi-layered object.

27. An apparatus for dynamic adjustment of a level of a response signal from an ultrasound transducer of an ultrasound system, the apparatus comprising:
a memory operable to store a plurality of gain profile descriptions, each gain profile description corresponding to a type of object to be tested by the ultrasound system;
a gain profile generator operable to generate a gain profile from the selected gain profile description of the plurality of gain profile descriptions; and
a level adjuster, responsive to the response signal, and operable to dynamically adjust the level of the response signal over time in accordance with the gain profile to produce a level adjusted response signal,
where the gain profile description is selected dependent upon user interaction with a user interface of the apparatus.

28. An apparatus in accordance with claim 27, wherein the memory stores a plurality of gain profile descriptions, each corresponding to a type of object, the apparatus further comprising:
a user interface operable to display a list of the object types to the user and receives information from the user; and
a selector operable to process the user input to select the gain profile from the plurality of gain profile descriptions.

29. An apparatus in accordance with claim 27, wherein the gain profile comprises a period of increasing gain and a period of decreasing gain.

30. An apparatus in accordance with claim 27, wherein the response signal comprises an echo of an excitation pulse.

31. An apparatus in accordance with claim 27, wherein the response signal corresponds to ultrasound transmitted through an object in response to an excitation pulse.

32. An ultrasound system comprising:
an input operable to receive a response signal from an ultrasonic transducer that senses ultrasound from an object under ultrasonic testing; and
an apparatus operable to dynamically adjust a level of the response signal, the apparatus comprising:
a user interface;
a gain profile selector operable to select a gain profile description dependent upon user interaction with the user interface;
a gain generator operable to generate a gain profile from the gain profile description; and
a level adjuster operable to adjust the level of the response signal dynamically in accordance with the gain profile,
the ultrasound system further comprising a memory operable to store a plurality of gain profile descriptions each corresponding to a type of object to be tested.

33. An ultrasound system in accordance with claim 32, wherein a gain profile description of the plurality of gain profile descriptions comprises a digital representation and wherein the level adjuster comprises a multiplying digital to analog converter.

34. An ultrasound system in accordance with claim 32, further comprising a controller operable to control the relative timing of the excitation waveform generator and the gain generator.

35. An ultrasound system in accordance with claim 32, further comprising an excitation waveform generator operable to supply an excitation waveform to an ultrasonic transducer that couples ultrasound to the object under ultrasonic testing.

36. An ultrasound system comprising:
an input operable to receive a response signal from an ultrasonic transducer that senses ultrasound from an object under ultrasonic testing; and
an apparatus operable to dynamically adjust a level of the response signal, the apparatus comprising:
a user interface;
a gain profile selector operable to select a gain profile description dependent upon user interaction with the user interface;
a gain generator operable to generate a gain profile from the gain profile description; and
a level adjuster operable to adjust the level of the response signal dynamically in accordance with the gain profile, the ultrasound system further comprising an excitation waveform generator operable to supply an excitation waveform to an ultrasonic transducer that couples ultrasound to the object under ultrasonic testing.

37. A method for ultrasonic imaging of a multi-layered object, comprising:
   exciting the multi-layered object with a pulse of ultrasound from an ultrasound transducer at a first time;
   sensing ultrasound produced by the multi-layered object in response to the pulse of ultrasound to obtain a response signal; and
   for each of a plurality of second times, subsequent to the first time, adjusting a level of the response signal in a level adjuster in accordance with a gain profile, to obtain a level adjusted response signal,
   wherein the plurality of second times corresponds to expected times of flight of ultrasound from layers of the multi-layered object.

38. A method in accordance with claim 37, further comprising:
   sampling the level adjusted response signal to obtain a sampled response signal; and
   processing the sampled response signal to obtain ultrasound images of at least one layer of the multi-layered object.

39. A method in accordance with claim 38, wherein the ultrasound images comprise ultrasound images of a plurality of layers of the multi-layered object and wherein processing the sampled response signal to obtain ultrasound images of the at least one layer of the multi-layered object comprises:
   for each pulse of ultrasound in a single scan:
      identifying a plurality of sections of the level adjusted response signal, the plurality of sections corresponding to reflections of ultrasound from a plurality of layers of the multi-layered object; and
      for each section of the plurality of sections:
         processing the level adjusted response signal in the section to update an ultrasound image of the plurality of ultrasound images.

40. A method in accordance with claim 37, further comprising selecting the gain profile to equalize sections of the level adjusted response signal corresponding to reflections of ultrasound from layers of the multi-layered object.

* * * * *